(12) United States Patent
Arad Hadar

(10) Patent No.: US 12,161,352 B2
(45) Date of Patent: *Dec. 10, 2024

(54) THROMBECTOMY DEVICE, SYSTEM AND METHOD FOR EXTRACTION OF VASCULAR THROMBI FROM A BLOOD VESSEL

(71) Applicant: ANACONDA BIOMED, S.L., Barcelona (ES)

(72) Inventor: Ofir Arad Hadar, Barcelona (ES)

(73) Assignee: ANACONDA BIOMED, S.L., Barcelona (ES)

( * ) Notice: Subject to any disclaimer, the term of this patent is extended or adjusted under 35 U.S.C. 154(b) by 304 days.

This patent is subject to a terminal disclaimer.

(21) Appl. No.: 17/235,764

(22) Filed: Apr. 20, 2021

(65) Prior Publication Data

US 2021/0236150 A1 Aug. 5, 2021

Related U.S. Application Data

(63) Continuation of application No. 15/649,266, filed on Jul. 13, 2017, now Pat. No. 11,013,523, which is a
(Continued)

(51) Int. Cl.
*A61B 17/22* (2006.01)
*A61B 17/12* (2006.01)
(Continued)

(52) U.S. Cl.
CPC .. *A61B 17/22031* (2013.01); *A61B 17/12031* (2013.01); *A61B 17/12109* (2013.01);
(Continued)

(58) Field of Classification Search
CPC ........ A61B 17/22031; A61B 17/12136; A61B 17/12031; A61B 17/12109;
(Continued)

(56) References Cited

U.S. PATENT DOCUMENTS

| 4,921,478 A | 5/1990 | Solano et al. |
| 5,011,488 A | 4/1991 | Ginsburg |

(Continued)

FOREIGN PATENT DOCUMENTS

| AU | 2018274903 B2 | 4/2020 |
| CN | 102973332 A | 3/2013 |

(Continued)

OTHER PUBLICATIONS

Bouthillier et al.; Segments of the internal carotid artery: a new classification; Neurosurgery; 38(3); pp. 425-433; Mar. 1, 1996.
(Continued)

*Primary Examiner* — Anh T Dang
(74) *Attorney, Agent, or Firm* — Shay Glenn LLP

(57) ABSTRACT

A thrombectomy device including a delivery catheter; a tapered dilator catheter configured to be movably disposed within the delivery catheter; and an expandable aspiration funnel configured to be movably disposed within the delivery catheter in a retracted position and at least partially outside the delivery catheter in an extended position, the funnel comprising a non-permeable covering, a diameter of a distal end of the funnel being greater in the extended position than in the retracted position, the funnel being configured to adapt its shape and length to a surrounding blood vessel such that the funnel lengthens as it narrows to retain a thrombus within the funnel. The invention also includes methods of using the device.

27 Claims, 4 Drawing Sheets

Related U.S. Application Data continuation-in-part of application No. PCT/EP2015/079400, filed on Dec. 11, 2015.

(51) Int. Cl.
   *A61B 17/221* (2006.01)
   *A61M 29/00* (2006.01)
   *A61B 17/00* (2006.01)
   *A61B 90/00* (2016.01)

(52) U.S. Cl.
   CPC ...... *A61B 17/12136* (2013.01); *A61B 17/221* (2013.01); *A61M 29/00* (2013.01); *A61B 2017/00867* (2013.01); *A61B 2017/00938* (2013.01); *A61B 2017/00942* (2013.01); *A61B 2017/1205* (2013.01); *A61B 2017/22051* (2013.01); *A61B 2017/2215* (2013.01); *A61B 2090/3966* (2016.02); *A61B 2217/007* (2013.01)

(58) Field of Classification Search
   CPC ...... A61B 2217/007; A61B 2017/1205; A61B 2017/2215; A61B 2017/22051; A61B 2017/00942; A61B 2017/00938; A61B 2017/00867; A61M 29/00; A61F 2/013
   See application file for complete search history.

(56) References Cited

U.S. PATENT DOCUMENTS

| | | |
|---|---|---|
| 5,102,415 A | 4/1992 | Guenther et al. |
| 5,190,561 A | 3/1993 | Graber |
| 5,605,530 A | 2/1997 | Fishell et al. |
| 5,769,871 A | 6/1998 | Mers Kelly et al. |
| 5,908,435 A | 6/1999 | Samuels |
| 5,971,938 A | 10/1999 | Hart et al. |
| 5,972,019 A | 10/1999 | Engelson et al. |
| 6,066,149 A | 5/2000 | Samson et al. |
| 6,159,230 A | 12/2000 | Samuels |
| 6,190,303 B1 | 2/2001 | Glenn et al. |
| 6,402,771 B1 | 6/2002 | Palmer et al. |
| 6,514,273 B1 | 2/2003 | Voss et al. |
| 6,663,650 B2 | 12/2003 | Sepetka et al. |
| 6,695,858 B1 | 2/2004 | Dubrul et al. |
| 6,730,104 B1 | 5/2004 | Sepetka et al. |
| 6,752,819 B1 | 6/2004 | Brady et al. |
| 7,004,954 B1 | 2/2006 | Voss et al. |
| 7,108,677 B2 | 9/2006 | Courtney et al. |
| 7,578,830 B2 | 8/2009 | Kusleika et al. |
| 7,686,825 B2 | 3/2010 | Hauser et al. |
| 7,993,302 B2 | 8/2011 | Hebert et al. |
| 8,088,140 B2 | 1/2012 | Ferrera et al. |
| 8,298,257 B2 | 10/2012 | Sepetka et al. |
| 8,679,142 B2 | 3/2014 | Slee et al. |
| 8,758,364 B2 | 6/2014 | Eckhouse et al. |
| 8,784,441 B2 | 7/2014 | Rosenbluth et al. |
| 8,858,497 B2 | 10/2014 | Di Palma et al. |
| 8,864,792 B2 | 10/2014 | Eckhouse et al. |
| 8,940,003 B2 | 1/2015 | Slee et al. |
| 8,984,003 B2 | 3/2015 | Ahmed et al. |
| 9,005,237 B2 | 4/2015 | Eckhouse et al. |
| 9,034,008 B2 | 5/2015 | Eckhouse et al. |
| 9,186,487 B2 | 11/2015 | Dubrul et al. |
| 9,463,035 B1 | 10/2016 | Greenhalgh et al. |
| 9,561,121 B2 | 2/2017 | Sudin et al. |
| 9,585,741 B2 | 3/2017 | Ma |
| 9,700,331 B2 | 7/2017 | Grandfield et al. |
| 9,844,381 B2 | 12/2017 | Eckhouse et al. |
| 9,861,783 B2 | 1/2018 | Garrison et al. |
| 10,285,720 B2 | 5/2019 | Gilvarry et al. |
| 10,292,804 B2 | 5/2019 | Wang et al. |
| 10,426,644 B2 | 10/2019 | Shrivastava et al. |
| 10,434,605 B2 | 10/2019 | Feth et al. |
| 11,013,523 B2 | 5/2021 | Jacobi et al. |
| 2003/0023299 A1 | 1/2003 | Amplatz et al. |
| 2003/0212430 A1 | 11/2003 | Bose et al. |
| 2003/0212439 A1 | 11/2003 | Schuler et al. |
| 2004/0024416 A1 | 2/2004 | Yodfat et al. |
| 2004/0073243 A1 | 4/2004 | Sepetka et al. |
| 2004/0098099 A1 | 5/2004 | McCullagh et al. |
| 2004/0143317 A1 | 7/2004 | Stinson et al. |
| 2004/0199201 A1 | 10/2004 | Kellett et al. |
| 2004/0243102 A1 | 12/2004 | Berg et al. |
| 2004/0260333 A1 | 12/2004 | Dubrul et al. |
| 2005/0209678 A1 | 9/2005 | Henkes et al. |
| 2006/0058838 A1 | 3/2006 | Bose et al. |
| 2006/0064073 A1 | 3/2006 | Schonholz et al. |
| 2006/0155305 A1 | 7/2006 | Freudenthal et al. |
| 2006/0293744 A1 | 12/2006 | Peckham et al. |
| 2007/0118165 A1 | 5/2007 | DeMello et al. |
| 2007/0188165 A1 | 8/2007 | Kitanaka et al. |
| 2007/0198028 A1 | 8/2007 | Miloslavski et al. |
| 2007/0203559 A1 | 8/2007 | Freudenthal et al. |
| 2007/0208367 A1 | 9/2007 | Fiorella et al. |
| 2007/0213765 A1 | 9/2007 | Adams et al. |
| 2007/0276332 A1 | 11/2007 | Bierman |
| 2007/0288038 A1 | 12/2007 | Bimbo |
| 2008/0228209 A1 | 9/2008 | DeMello et al. |
| 2008/0269774 A1 | 10/2008 | Garcia et al. |
| 2008/0269798 A1 | 10/2008 | Ramzipoor et al. |
| 2009/0163846 A1 | 6/2009 | Aklog et al. |
| 2009/0198269 A1 | 8/2009 | Hannes et al. |
| 2010/0004607 A1 | 1/2010 | Wilson et al. |
| 2010/0030256 A1 | 2/2010 | Dubrul et al. |
| 2010/0222864 A1 | 9/2010 | Rivelli et al. |
| 2011/0160763 A1 | 6/2011 | Ferrera et al. |
| 2011/0213297 A1 | 9/2011 | Aklog et al. |
| 2012/0059309 A1 | 3/2012 | Di Palma et al. |
| 2012/0065660 A1 | 3/2012 | Ferrera et al. |
| 2012/0083868 A1 | 4/2012 | Shrivastava et al. |
| 2012/0114017 A1 | 5/2012 | Bang et al. |
| 2012/0116440 A1 | 5/2012 | Leynov et al. |
| 2012/0179181 A1 | 7/2012 | Straub et al. |
| 2013/0261638 A1 | 10/2013 | Diamant et al. |
| 2013/0325055 A1 | 12/2013 | Eckhouse et al. |
| 2013/0325056 A1 | 12/2013 | Eckhouse et al. |
| 2014/0052161 A1 | 2/2014 | Cully et al. |
| 2014/0074144 A1 | 3/2014 | Shrivastava et al. |
| 2014/0155908 A1 | 6/2014 | Rosenbluth et al. |
| 2014/0243885 A1 | 8/2014 | Eckhouse et al. |
| 2014/0277015 A1 | 9/2014 | Stinis |
| 2015/0112376 A1 | 4/2015 | Molaei et al. |
| 2015/0157346 A1 | 6/2015 | Ferrera et al. |
| 2015/0164666 A1 | 6/2015 | Johnson et al. |
| 2015/0231360 A1 | 8/2015 | Watanabe et al. |
| 2015/0359547 A1 | 12/2015 | Vale et al. |
| 2016/0081704 A1 | 3/2016 | Jeon et al. |
| 2016/0256255 A9 | 9/2016 | Ma |
| 2017/0007164 A1 | 3/2017 | Vale et al. |
| 2017/0065299 A1 | 3/2017 | Gillespie et al. |
| 2017/0105743 A1 | 4/2017 | Vale et al. |
| 2017/0119408 A1 | 5/2017 | Ma |
| 2017/0119409 A1 | 5/2017 | Ma |
| 2017/0215900 A1 | 8/2017 | Lowinger et al. |
| 2017/0215902 A1 | 8/2017 | Leynov et al. |
| 2017/0239444 A1 | 8/2017 | Parker |
| 2017/0333060 A1 | 11/2017 | Panian |
| 2018/0028209 A1 | 2/2018 | Sudin et al. |
| 2018/0064454 A1 | 3/2018 | Losordo et al. |
| 2018/0126132 A1 | 5/2018 | Heilman et al. |
| 2018/0132876 A1 | 5/2018 | Zaidat |
| 2018/0206862 A1 | 7/2018 | Long |
| 2018/0318062 A1 | 11/2018 | Sudin et al. |
| 2018/0353196 A1 | 12/2018 | Epstein et al. |
| 2018/0361114 A1 | 12/2018 | Chou et al. |
| 2019/0110805 A1 | 4/2019 | Ulm, III |
| 2019/0167284 A1 | 6/2019 | Friedman et al. |
| 2019/0167287 A1 | 6/2019 | Vale et al. |
| 2019/0216476 A1 | 7/2019 | Barry et al. |
| 2019/0239907 A1 | 8/2019 | Brady et al. |
| 2019/0269425 A1 | 9/2019 | Sudin et al. |
| 2019/0298396 A1 | 10/2019 | Gamba et al. |
| 2019/0307471 A1 | 10/2019 | Friedman et al. |

(56) References Cited

U.S. PATENT DOCUMENTS

| | | |
|---|---|---|
| 2019/0336727 A1 | 11/2019 | Yang et al. |
| 2020/0000613 A1 | 1/2020 | Shrivastava et al. |
| 2020/0008822 A1 | 1/2020 | Eckhouse et al. |
| 2021/0000582 A1 | 1/2021 | Chomas et al. |
| 2021/0077134 A1 | 3/2021 | Vale et al. |
| 2022/0117614 A1 | 4/2022 | Salmon et al. |
| 2023/0127145 A1 | 4/2023 | Arad Hadar et al. |

FOREIGN PATENT DOCUMENTS

| | | |
|---|---|---|
| CN | 104159525 A | 11/2014 |
| CN | 107198554 B | 2/2020 |
| EP | 1427087 A1 | 6/2004 |
| EP | 2662109 A1 | 11/2013 |
| EP | 3266391 A1 | 1/2018 |
| ES | 2341978 T3 | 6/2010 |
| ES | 2381099 T3 | 5/2012 |
| GB | 2498349 A | 7/2013 |
| JP | 2005500138 A | 1/2005 |
| WO | WO99/45835 A2 | 9/1999 |
| WO | WO02/087677 A2 | 11/2002 |
| WO | WO03/075793 A1 | 9/2003 |
| WO | WO2004/002564 A1 | 1/2004 |
| WO | WO2005/027751 A1 | 3/2005 |
| WO | WO2008/124567 A1 | 10/2008 |
| WO | WO2008/157202 A1 | 12/2008 |
| WO | WO2009/014723 A1 | 1/2009 |
| WO | WO2009/105710 A1 | 8/2009 |
| WO | WO2011/068924 A1 | 6/2011 |
| WO | WO2011/082319 A1 | 7/2011 |
| WO | WO2012/106657 A2 | 8/2012 |
| WO | WO2012/156924 A1 | 11/2012 |
| WO | WO2012/158269 A1 | 11/2012 |
| WO | WO2013/008233 A1 | 1/2013 |
| WO | WO2013/152327 A1 | 10/2013 |
| WO | WO2014/008460 A2 | 1/2014 |
| WO | WO2014/127389 A2 | 8/2014 |
| WO | WO2014/204860 A1 | 12/2014 |
| WO | WO2015/006782 A1 | 1/2015 |
| WO | WO2015/189354 A1 | 12/2015 |
| WO | WO2016/113047 A1 | 7/2016 |
| WO | WO2017/072663 A1 | 5/2017 |
| WO | WO2017/074290 A1 | 5/2017 |
| WO | WO2017/075544 A1 | 5/2017 |
| WO | WO2018/080590 A1 | 5/2018 |
| WO | WO2018/160966 A1 | 9/2018 |

OTHER PUBLICATIONS

Rios Garriga et al.; U.S. Appl. No. 17/621,717 entitled "Delivery catheter device and system for accessing the intracranial vasculature," filed Dec. 22, 2021.

Duffy et al.; Novel methodology to replicate clot analogs with diverse composition in acute ischemic stroke; Journal of neurointerventional surgery; 9(5); pp. 486-491; May 1, 2017.

Fennell et al.; What to do about fibrin rich tough clots? Comparing the Solitaire stent retriever with a novel geometric clot extractor in an in vitro stroke model; Journal of neurointerventional surgery; 10(9); pp. 907-910; Sep. 1, 2018.

Mokin et al.; Stent retriever thrombectomy with the Cover accessory device versus proximal protection with a balloon guide catheter: in vitro stroke model comparison; Journal of neurointerventional surgery; 8(4); pp. 413-417; Apr. 1, 2016.

Arad Hadar et al.; U.S. Appl. No. 17/291,696 entitled "A thrombectomy system and methods of extracting a thrombus from a thrombus site in a blood vessel of a patient," filed May 6, 2021.

Ros Fàbrega et al.; U.S. Appl. No. 17/415,866 entitled "Loading device for loading a medical device into a catheter," filed Jun. 18, 2021.

Berkhemer et al.; A randomized trial of intraarterial treatment for acute ischemic stroke; New England Journal of Medicine; 372; pp. 11-20; Jan. 1, 2015.

Ceretrieve; 3 pages; retrieved from the internet (http://trendlines.com/portfolio/ceretrieve/) on Sep. 13, 2018.

Cortinas Villazon et al.; U.S. Appl. No. 17/274,973 entitled "A device and a thrombectomy apparatus for extraction of thrombus from a blood vessel," filed Mar. 10, 2021.

Castano et al.; Unwanted detachment of the Solitaire device during mechanical thrombectomy in acute ischemic stroke; Journal of neurointerventional surgery; 8(12); pp. 1226-1230; Dec. 1, 2016.

Penumbra Inc.; Recalls 3D revascularization device due to wire material that may break or separate during use; FDA Recall; retrieved from the internet (http://web.archive.org/web/20200813123505/https:/www.fda.gov/medical-devices/medical-device-recalls/penumbra-inc-recalis-3d-revascularization-device-due-wire-material-may-break-or-separate-during-use).

Garcia-Sabido et al.; U.S. Appl. No. 18/040,492 entitled "A clot mobilizer device for extraction of an occlusion from a blood vessel," filed Feb. 3, 2023.

Garcia-Sabido et al.; U.S. Appl. No. 18/040,495 entitled "An elongated device with an improved attachment of its elements," filed Feb. 3, 2023.

Salmon et al; U.S. Appl. No. 18/447,854 entitled "Thrombectomy system and method of use," filed Aug. 10, 2023.

Garcia Sabido et al; U.S. Appl. No. 18/546,190 entitled "An expandable clot mobilizer device for extraction of an occlusion from a blood vessel," filed Aug. 11, 2023.

Garcia Sabido et al.; U.S. Appl. No. 18/546,206 entitled "A self expandable medical device for advancement through vasculature to an expansion site in a blood vessel," filed Aug. 11, 2023.

Medtronic; Medtronic.com; The Solitaire Platinum Revascularization Device; Model Specifications; DC00079632 Rev A ; 1 page; retrived from the internet (https//www.medtronic.com) on Mar. 2018.

FIG. 7C
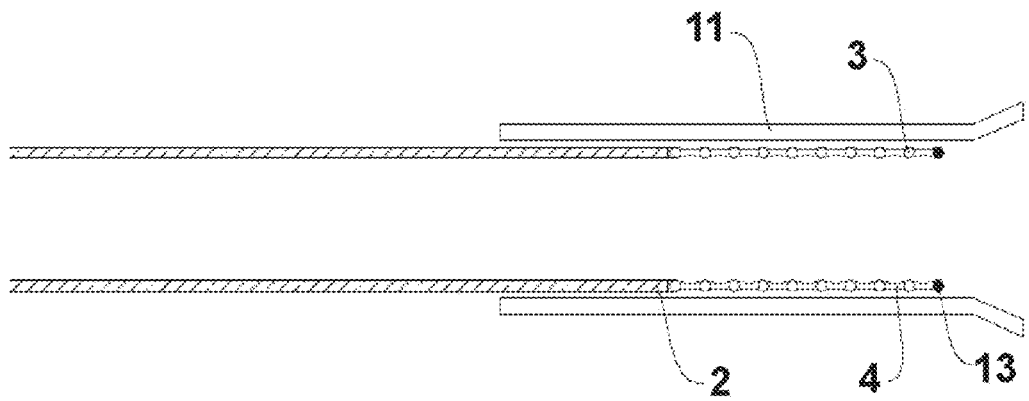
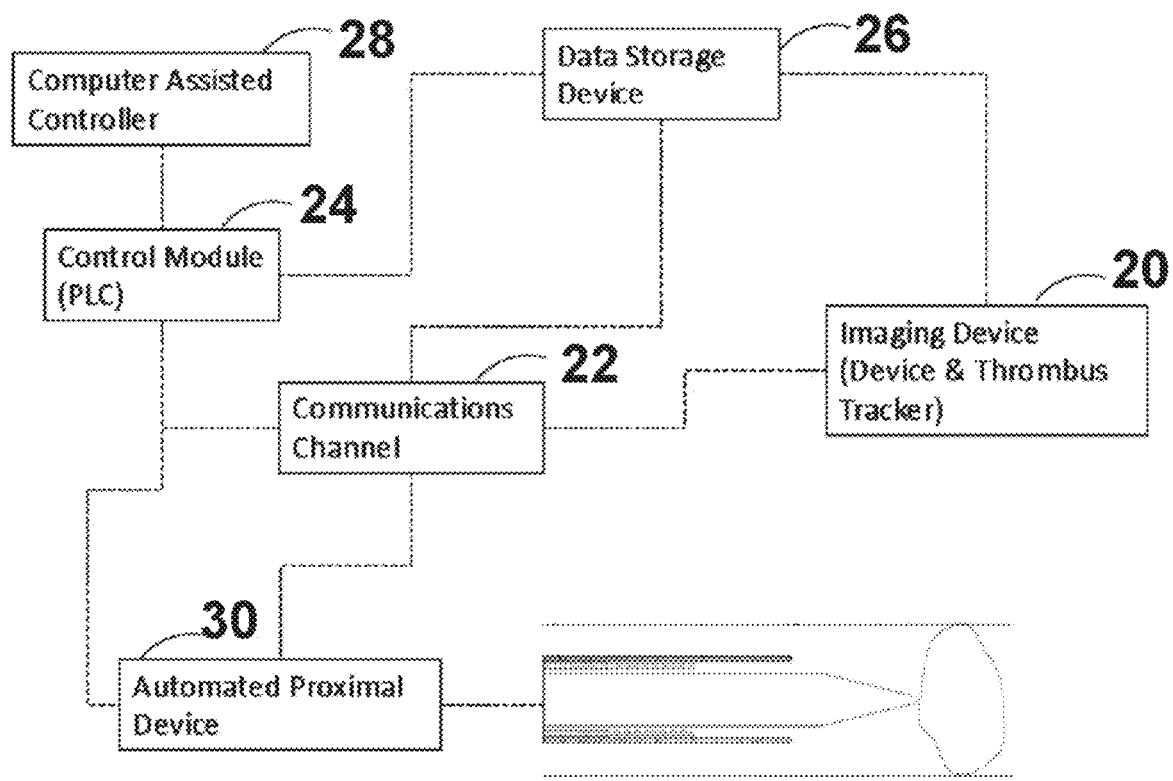
FIG. 8

THROMBECTOMY DEVICE, SYSTEM AND METHOD FOR EXTRACTION OF VASCULAR THROMBI FROM A BLOOD VESSEL

CROSS REFERENCE TO RELATED APPLICATIONS

This application is a continuation of U.S. application Ser. No. 15/649,266, filed Jul. 13, 2017, which is a continuation-in-part of PCT/EP2015/079400, filed Dec. 11, 2015, which claims priority to Spanish Application No. P201530028, filed Jan. 13, 2015, each of which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE DISCLOSURE

The present invention relates to a thrombectomy device that allows extraction of vascular thrombi and to a system for extraction of vascular thrombi from a blood vessel.

Endovascular treatment has been employed in cases of stroke since the 1990s. The number of patients it has been used on has grown slowly but steadily. The main obstacle for wide use of these highly complex treatments is the need for a more coordinated medical system, at various levels. The main goal of these medical networks is to ensure that patients can get to centers with required capabilities within 6-8 hours of symptom onset.

Recently, the first positive randomized study was published (Berkhemer O. A. et al. "A randomized trial of intraarterial treatment for acute ischemic stroke." N Engl J Med. January 2015; 372: 11-20. doi: 10.1056/NEJMoa141 1587. Epub 17 Dec. 2014. PubMed PMID: 25517348) demonstrating the efficacy of the thrombectomy treatment as compared to more conventional medical treatments by reducing the disability rate three months after a stroke. In addition, four other major similar clinical trials were published in 2015 definitively confirming the superiority of thrombectomy treatment with latest-generation devices by reducing impairment as compared to other medical treatments.

With regard to endovascular treatment, initially the strategy was local perfusion of a fibrinolytic agent through a microcatheter directly into the thrombus. In the early 2000s, a new device was introduced that appeared to be more effective than intraarterial fibrinolysis. It was a spiral that opened around the thrombus, facilitating its extraction (MERCI®). In 2006, a system basically based on bringing a large-gauge catheter in close proximity to the thrombus in order to aspirate it became popular. The catheter is connected to a continuous aspiration pump (Penumbra®). This system has evolved over the years, seeking to attain a catheter with an increasingly large diameter, able to navigate close to the thrombus.

The use of the so-called stent retrievers began around 2009. Their use consists of crossing the thrombus with a microcatheter, then advancing the stent through the microcatheter. Once the distal end of the sheathed device has reached the most distal part of the thrombus, the stent is unsheathed, self-expanding at the thrombus level and captures the thrombus. It is advisable to wait several minutes with the stent expanded to increase the engagement of the thrombus and then withdraw the expanded stent with the intention of it dragging the thrombus. This final step can be done while aspirating through the catheter to try to reverse the flow and thus increase the chances of recovering the thrombus. Stent retrievers have entirely displaced the first-generation devices described above due to their high efficacy, case to use and reduced procedure times.

In addition, when using a stent retriever, a guide balloon catheter is often used. This catheter only advances to the extracranial carotid (distant from thrombi located in the intracranial arteries). Upon inflation of the balloon situated at the end of the catheter, the catheter is able to stop the flow in the arterial segment distal to the balloon, which is where the thrombus to be extracted is located. By aspirating through it, the flow in the arterial segment distal to the balloon can be reversed in order to facilitate the removal of the thrombus together with the stent retriever.

In summary, there are currently two trends in the use of thrombectomy devices: on one hand the so-called stent retrievers (with or without balloon catheter), and on the other hand devices based on an aspiration catheter (with manual aspiration with syringe or automatic aspiration with aspiration pump). The two techniques can be combined.

An example of a thrombectomy device is described in WO2011/082319, with a variety of interchangeable tips according to the needs of the surgeon during thrombectomy procedure. In all cases, the device described in this document has to cross the interior of the thrombus or pass between the thrombus and the arterial wall before being expanded. Furthermore, in all cases the thrombus must be fragmented to be dissolved by natural or artificial means. As result of these operational principles, this device does not allow the removal of the thrombus in a way that ensures there will be no distal embolization due to a release of clot fragments.

WO 02/087677 A2 discloses an apparatus and methods used to prevent the introduction of emboli into the bloodstream during and after surgery performed to reduce or remove blockage in blood vessels.

Furthermore, unlike the device of the present invention, it does not have a covered distal end, and, therefore, it is unable to stop the flow of the artery, much less reverse it.

Additionally, stent-retrievers of the present art will, upon deployment, need time (up to three minutes) to acclimatize to the thrombus prior to retrieving the thrombus to minimize fracturing of the thrombus. When dealing with a potential stroke, time is of the essence, and the current device can be used to retrieve the thrombus immediately upon arrival by aspiration.

Therefore, the device according to the present invention is intended to replace aspiration devices, improving on their effectiveness, since it will allow aspiration from a very close proximity to the thrombus and with a large mouth, allowing occlusion of the artery, stopping the flow, and aspirating the entire thrombus without fragmenting it.

The present invention may be used by itself to cut off blood flow, aspirate the thrombus, and remove the thrombus; which means that a physician does not need additional devices to complete these tasks.

An automated embodiment of the present invention also may be used in both traditional (hospital) and non-traditional (nursing home, assisted care facility) environments which may allow for greater deployment and usage of the present invention and hasten the removal of the thrombus, thus significantly improving patient outcomes, as blood flow may be restored in critical areas of the brain within much shorter times.

SUMMARY OF THE DISCLOSURE

The device and system of the present invention manages to resolve the aforesaid disadvantages, providing other advantages that will be described below.

One aspect of the invention provides a thrombectomy device having a delivery catheter; a tapered dilator catheter configured to be movably disposed within the delivery catheter; and an expandable aspiration funnel configured to be movably disposed within the delivery catheter in a retracted position and at least partially outside the delivery catheter in an extended position, the funnel comprising a non-permeable covering, a diameter of a distal end of the funnel being greater in the extended position than in the retracted position, the funnel being configured to adapt its shape and length to a surrounding blood vessel such that the funnel lengthens as it narrows to retain a thrombus within the funnel.

In some embodiments, the aspiration funnel is configured to remain within the delivery catheter after the dilator catheter has been removed. In some embodiments, the funnel is configured to be self-expandable, and in some embodiments, the funnel is configured to be manually expanded, and the device may further include a balloon catheter adapted to expand the funnel.

In some embodiments, the funnel has a diameter at its distal end of between 2 millimeters and 15 millimeters. The funnel may also include a thrombus retaining element, such as a sharp physical element.

In some embodiments, the delivery catheter, dilator catheter and funnel are oriented on the same axis. Some embodiments may also include a resheathing element adapted to reintroduce the funnel into the delivery catheter.

Another aspect of the invention provides a method of extracting a thrombus from a thrombus site in a blood vessel of a patient, with the method including the following steps: advancing a delivery catheter, a tapered dilator catheter and an aspiration funnel through vasculature of the patient toward the thrombus site with a distal end of the tapered dilator catheter disposed distal to a distal end of the delivery catheter and the aspiration funnel disposed in a retracted position proximal to the distal end of the delivery catheter; retracting the dilator catheter into the delivery catheter; moving the aspiration funnel and delivery catheter with respect to each other to place the aspiration funnel in an extended position at least partially outside of the delivery catheter; occluding the blood vessel with the funnel to stop flow of blood in the blood vessel; aspirating the thrombus into the funnel; moving the funnel and the thrombus proximally within the vasculature; and adapting a shape and length of the funnel to a surrounding blood vessel of the vasculature such that the funnel lengthens as it narrows to retain the thrombus within the funnel.

In some embodiments, the occluding step includes the step of expanding a distal end of the funnel to a diameter of the blood vessel proximal to the thrombus site.

In some embodiments, the moving step includes the step of expanding a distal end of the funnel.

In some embodiments, the expanding step includes the step of allowing the funnel to self-expand. In some embodiments, the expanding step includes the step of decreasing a length of the funnel.

In some embodiments, the advancing step includes the step of advancing the delivery catheter, the tapered dilator catheter and the aspiration funnel along a common axis.

Some embodiments also include the step of moving the funnel proximally into the delivery catheter after the aspirating step.

The thrombectomy device according to yet another aspect of the invention comprises a delivery catheter, a dilator catheter and a funnel, defining a distal end and a proximal end, said funnel being positionable in a retracted position and in an extended position, and said funnel also comprises a covering, the diameter of the distal end of the funnel being greater in the extended position than in the retracted position. In the extended position the dilator catheter is removed and the funnel is ready to allocate a thrombus when aspired.

In one embodiment, said covering is a non-permeable film, e.g., made from one or a combination of more than one biocompatible elastomeric polymers or other plastics materials, such as expanded polytetrafluoroethylene (ePTFE) or biocompatible polyurethane with elastomeric behavior which facilitates the resheathing of the said funnel. Said covering can also comprise polymer fibers oriented parallel to the direction of the length of the dilator catheter.

Furthermore, said funnel may be positioned inside the delivery catheter in the retracted position and is positioned at least partially outside the delivery catheter in the extended position.

Said funnel may be made of metals or metallic alloys, polymers, ceramics or combinations of them. Said funnel may be made from shape-memory materials, such as, e.g., nitinol. In some embodiments, the funnel is self-expandable. In other embodiments, the funnel is expanded with mechanical means such as, e.g., a single catheter balloon or a set of catheter balloons.

In some embodiments, the funnel can expand to a diameter of between about 2 millimeters and 15 millimeters. Said funnel, delivery catheter, and/or dilator catheter can comprise at least one radiopaque marker, e.g., at distal end. The funnel may also have a lubricious hydrophilic or hydrophobic coating. In some embodiments, the funnel includes a retaining means for retaining a thrombus, such as sharp physical elements such as spikes, skewers, saws, clamps or any combination of them.

In some embodiments, said covering, delivery catheter, dilator catheter and/or funnel can comprise a lubricious hydrophilic or hydrophobic coating.

Furthermore, in some embodiments, said funnel shortens as the diameter of the funnel expands. The delivery catheter, the dilator catheter, and the funnel may be oriented along the same axis in some embodiments.

The device according to the present invention can also comprise a resheathing element, such as, e.g., a cannula, a clamp, a funnel or any combination of them, for reintroducing the funnel into the delivery catheter.

Said funnel is expanded to blood vessel diameter in order to enable occlusion of the proximal flow and, even, flow reversal upon aspiration through the device, thus facilitating the extraction of the thrombus with a very short dragging distance and with the ability to capture the entire thrombus inside it without fragmentation.

The present invention also refers to a system for extraction of vascular thrombi from a blood vessel comprising a thrombectomy device as described previously; a communications channel, a control module, a data storage device, and a guidance system.

Said system can also comprise an imaging device, a first radiomarker, and a second radiomarker, wherein said first radiomarker indicating the location of the distal end of the funnel, and said second radiomarker indicating the location of the vascular thrombus, and a computer assisted controller.

BRIEF DESCRIPTION OF THE DRAWINGS

For a better understanding of the foregoing, several drawings are attached, which schematically and solely by way of non-limiting example represent a practical case of the embodiment.

FIGS. 7A, 7B, and 7C present schematic elevational views of a thrombectomy device with a retractor according to the present invention depicting the device in which the device is in several different positions.

FIG. 8 is a diagram depicting an automated thrombectomy system according to the present invention.

DETAILED DESCRIPTION

The thrombectomy device according to the present invention is particularly suited to remove a thrombus from an intracranial artery without causing or allowing the thrombus to fragment and without causing damage to the intracranial artery thus avoiding development of additional thrombi. Though the device is particularly suited for removal of intracranial artery thrombi, it may be used to remove a thrombus in any artery or vein.

Figure 1:
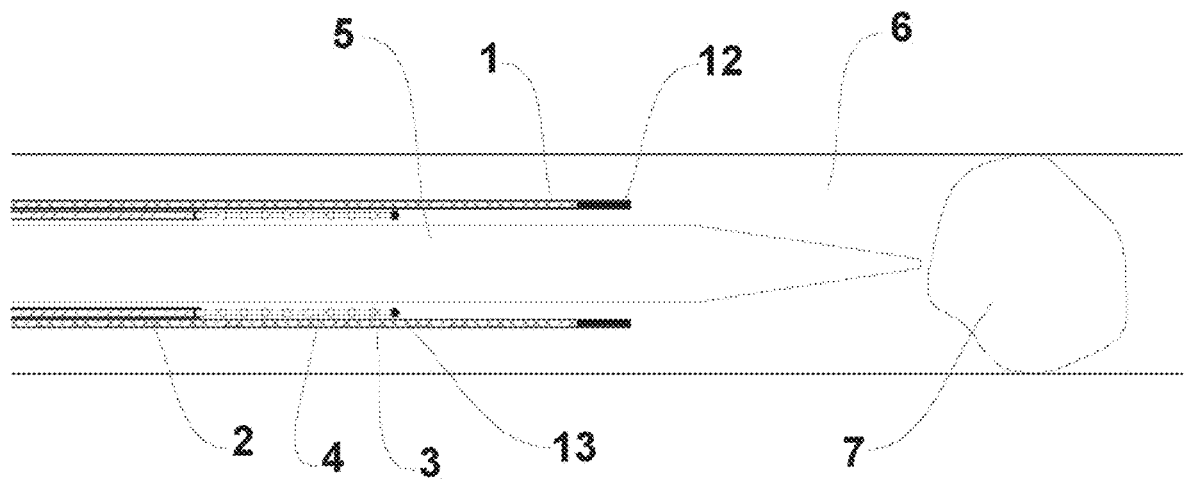
FIG. 1 is a schematic elevational view of the thrombectomy device according to the present invention in its approaching configuration, which is used for clearing the way through blood vessels and reaching the artery where the thrombus is located.
Figure 2:
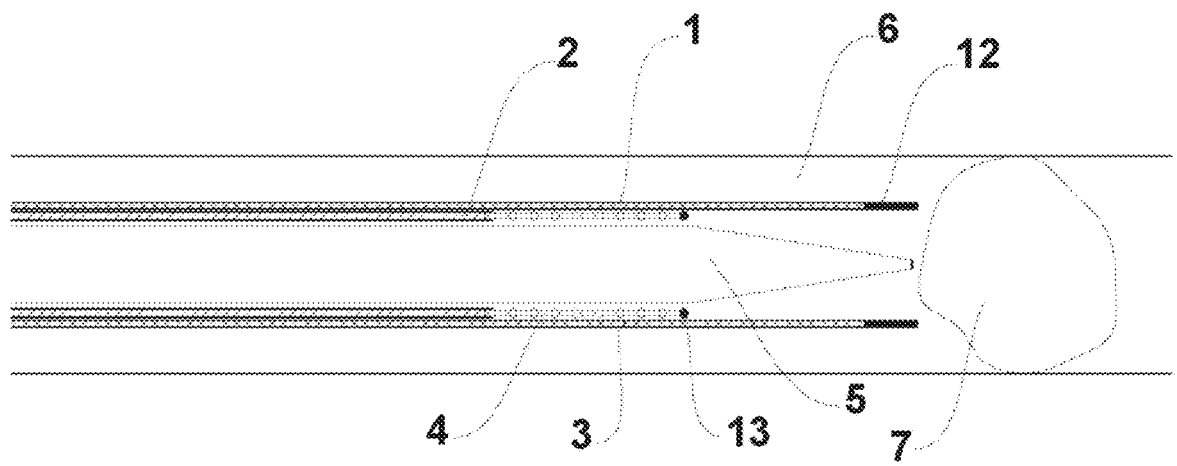
FIG. 2 is a schematic elevational view of the thrombectomy device according to the present invention in its retracted or navigational configuration, used to navigate the delivery catheter (carrying inside it the aspiration funnel catheter) to the face of the thrombus.
Figure 3:
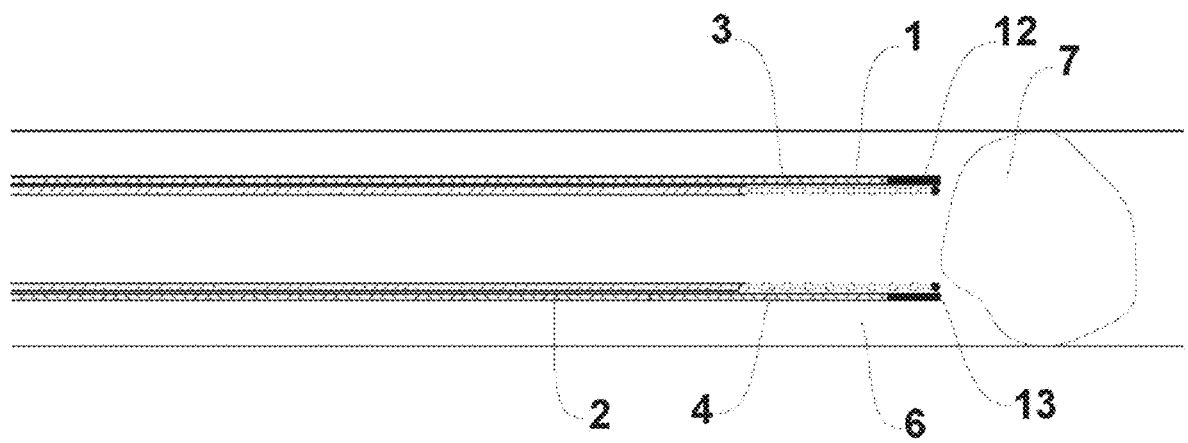
FIG. 3 is a schematic elevational view of the thrombectomy device according to the present invention in its aligned or ready-to-expand configuration, ready to deliver the aspiration funnel.
Figure 4:
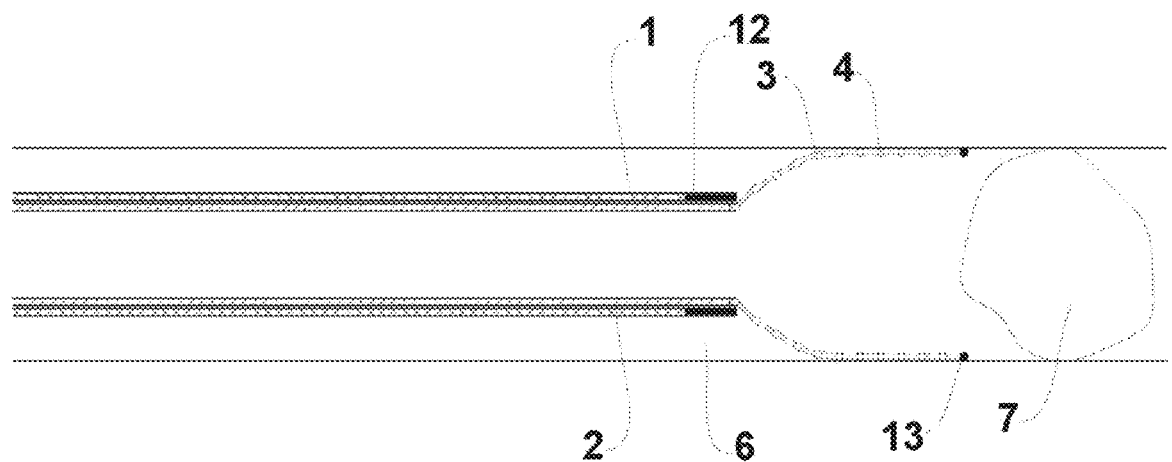
FIG. 4 is a schematic elevational view of the thrombectomy device according to the present invention in its expanded or ready-to-aspirate configuration, when the funnel adapts itself to the vessel shape and faces the thrombus before it is aspirated.

In one embodiment, the thrombectomy device according to the present invention comprises a tapered dilator catheter 5, an aspiration funnel catheter 2 (composing a covered stent 3 and a pusher element, such as a hypotube shaft) and a delivery catheter 1, each with the definition of a distal end and a proximal end. This device has four different configurations: 1) an approaching configuration with the tapered dilator catheter 5 well ahead from other elements of the device and navigating through blood vessels and reaching the thrombus 7 to be removed as depicted in FIG. 1; 2) a retracted or navigational configuration with aspiration funnel 2 retracted (no expansion) inside the delivery catheter 1 and proximally fixed at some distance from the distal end of the delivery catheter 1, in such configuration the device displays an enhanced navigability and pushability for reaching the thrombus 7 as depicted in FIG. 2; 3) an aligned or ready-to-expand configuration with the distal end of the covered funnel 3 and distal end of delivery catheter 1 aligned and in contact with the thrombus 7 as depicted in FIG. 3; and 4) an expanded or ready-to-aspirate configuration with the covered funnel 3 expanded to the vessel 6 diameter and in close contact with the thrombus 7, delivery catheter 1 proximally fixed at some distance from the distal end of the funnel 3 and the tapered dilator catheter 5 removed, in such configuration the diameter of the funnel 3 distal end is greater than in the previous configurations and it is ready to allocate thrombus 7 when aspired as depicted in FIG. 4.

Advantageously, said funnel 3 is positioned inside the delivery catheter 1 in the retracted or navigational configuration and in the aligned or ready-to-expand configuration and is positioned at least partially outside the delivery catheter 1 in the expanded or ready-to-aspirate configuration.

In accordance with a preferred embodiment, the funnel 3 is a stent covered with a non-permeable film. This stent has a variable diameter, able to expand to the diameter of the blood vessel 6 at a point proximal to the thrombus 7, thus being able to stop the flow and capture the entire thrombus 7 inside it, without needing to fragment it. The stent may be self-expandable but may also be expanded by other mechanisms such as an inflated balloon in its interior.

The funnel 3 skeleton may be made of shape-memory materials: metals (including metallic alloys), polymers, ceramics or whatever combination of them with suitable mechanical properties. In accordance with one embodiment, said skeleton is a stent made of Nitinol™ (a 50 percent nickel/50 percent titanium alloy, NiTi). This skeleton can include radiopaque markers 13 at its distal end and other strategic points which allow the physician to know the precise location of the device while using fluoroscopy. The funnel 3 may have a covering, said funnel covering 4 is a non-permeable film made of one or combination of more than one biocompatible materials. In accordance with one embodiment, said funnel covering 4 is a biocompatible polymer, elastomeric or other suitable plastic material. In one embodiment, the said polymer is a durable biocompatible polyurethane with elastomeric behavior, which allows funnel 3 resheathing when required. In another preferred embodiment, said funnel covering 4 is expanded polytetrafluoroethylene (ePTFE) with the polymer fibers oriented parallel to the direction of the length of the catheter 1, and thus with reduced or almost no resistance to expansion and reduced or almost no funnel recoiling without application of an external force.

The expandable covered distal end of the device according to this invention allows artery blood flow to be stopped and even reversed when combined with vacuum. It is thereby possible to aspirate the entire thrombus 7, and minimize and even prevent the detachment of fragments during the procedure or during withdrawal of the device.

Depending upon the specifics of an individual thrombectomy, the funnel 3 of the device described on the present invention can be resheathed within the delivery catheter 1 before, during and after the removal of the thrombus 7. That is, the device allows for the resheathing of the funnel 3 at any time during the procedure, even while the thrombus 7 is being extracted.

Another relevant feature of the device of the present invention is that it is not intended to cross or compress the thrombus 7. Thus, it has the advantage of ensuring the removal of the entirety of the thrombus 7, thus avoiding a possible distal embolization.

Furthermore, said funnel 3 is intended and able to adapt its shape and its length to the surrounding blood vessel 6 so, in the case of encountering a narrow passage during the device removal while carrying the thrombus 7, changes in funnel 3 shape encompass any dimensional change on the thrombus 7, avoiding any leak of thrombus material. While passing through the narrow passage, as the funnel 3 narrows proportionally it also lengthens allowing for the entire thrombus 7 to remain securely within the funnel 3.

Figure 5:
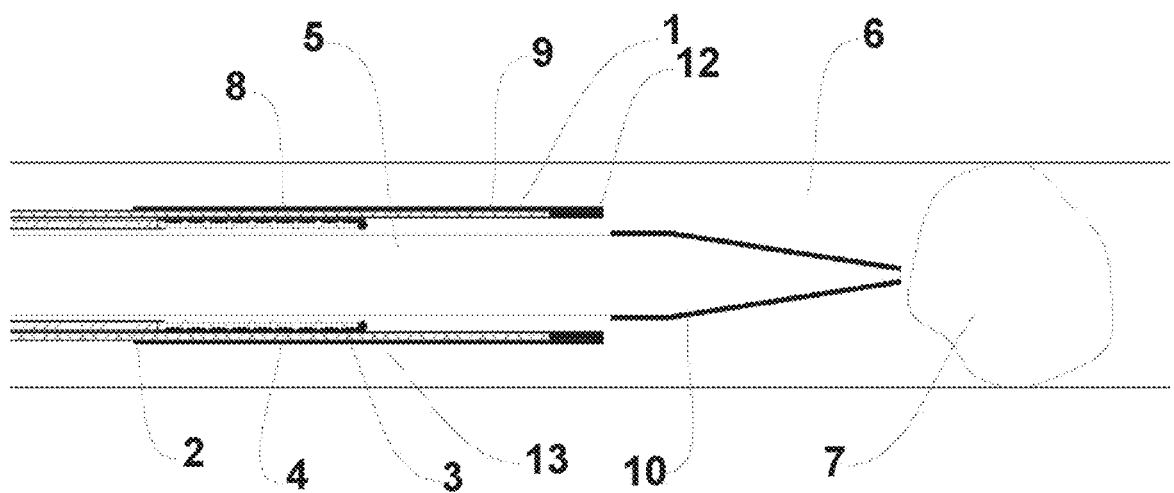
FIG. 5 is a schematic elevational view of the thrombectomy device according to the present invention depicting the entire device in its deploying configuration, including all the device components and depicting points with hydrophilic coating.

FIG. 5 shows the thrombectomy device according to the present invention, which comprises a tapered dilator catheter 5, an aspiration funnel 3 and a delivery catheter 1.

To facilitate the description, the ends of the device are defined as the distal end and the proximal end, with the distal end being the farthest from the user manipulating the device according to the present invention and, therefore, the closest to the thrombus 7 to be removed, and the proximal end being the end closest to the user and, therefore, the farthest from the thrombus 7.

The thrombectomy device according to the present invention can be in four different configurations: approaching configuration (shown in FIG. 1), retracted or navigational configuration (shown in FIG. 2), aligned or ready-to-expand configuration (shown in FIG. 3) and expanded or ready-to-aspirate configuration (shown in FIG. 4), as will be explained below, with the diameter of the distal end of the funnel 3 greater in the expanded configuration than in any other.

In the retracted and aligned configurations, said funnel 3 is positioned inside the delivery catheter 1, while in the expanded configuration it is positioned at least partially outside of the delivery catheter 1.

In accordance with one embodiment, said funnel 3 is a stent with a non-permeable film covering. The stent funnel 3 may be self-expandable but may also be expanded by other mechanisms such as an inflated balloon in its interior.

The funnel 3 may be made of any material with shape-memory properties, including metals (even metallic alloys), polymers, ceramics or combination thereof with suitable mechanical properties, and said funnel 3 can have radiopaque markers 13 at its distal end and other strategic points. In accordance with one embodiment, the funnel 3 is made of Nitinol™. Thus, the distal end of the funnel 3 expands upon unsheathing, as it has shape memory and it is self-expandable, and when the funnel 3 exits the delivery catheter 1 at body temperature its natural tendency will be to expand. It should be noted, however, that this expansion can be effected by other systems, e.g., by inflating a balloon of the required diameter in its interior. Furthermore, the said funnel covering 4 is a non-permeable film made of one or combination of more than one biocompatible materials. In accordance with one embodiment, said covering 4 is a biocompatible polymer, elastomeric or other suitable plastic material. In one embodiment, said polymer is a durable biocompatible polyurethane with elastomeric behavior, which allows funnel 3 resheathing when required. In another preferred embodiment, said covering 4 is expanded polytetrafluoroethylene (ePTFE) with the ePTFE polymer fibers oriented parallel to the direction of the length of the catheter 1, and thus with reduced or almost no resistance to expansion and reduced or almost no funnel 3 recoiling without application of an external force.

In one embodiment of the present invention, said covering 4 can have a lubricious coating 8 (hydrophilic or hydrophobic) and so may other strategic points of every device component, for example catheter tips 9, 10 (shown in FIG. 5). Referring again to FIG. 4, in one embodiment of the invention the distal funnel 3 is self-expanding. In other embodiments of the present invention, the expansion of the funnel 3 may be accomplished through various mechanical means including usage of a balloon. Advantageously, the expansion of the funnel 3 will enable occlusion of the proximal flow, reversal by aspiration of the flow at the distal arterial segment, a very short thrombus dragging distance and the ability to capture the entire thrombus 7 inside it without fragmentation, facilitating the extraction thereof.

As depicted in FIGS. 3 and 4, another feature of the self-expandable stented funnel 3 is that the funnel 3 shortens as the funnel 3 expands to the diameter of the blood vessel 6. This decrease in funnel 3 length is inversely proportional to the arterial diameter, that is: the funnel 3 length is shorter in a 5-millimeter diameter artery than in a 2 millimeter diameter artery. Even more advantageously, the self-expandable stented funnel 3 spreads the radial force loaded over the arterial wall over its entire length, thanks to the precise combination of the self-expandable funnel 3 and the biocompatible no permeable film between its struts. In that way, it can be assured that the total pressure exerted on the arterial wall remains constant in all arteries with a diameters between about 2 mm and 15 mm (both inclusive), or between about 2 mm and 6 mm.

The device of the present invention bears a superior aspiration power and enables the retrieval of thrombus of multiples sizes, shapes and dimensions thanks to its versatile aspiration funnel. In fact, any of the foreseen configurations of the said funnel is intended to adjust to the vessel walls and its geometry, and to adopt the to the vessel diameter (up to 5.9 mm. 0.232"): this particular feature of the device makes possible to aspirate bigger thrombus and with higher vacuum power than other marketed devices (e.g., Navien 0.064", Penumbra 0.072"). In one embodiment of the present invention, the aspiration funnel catheter 2 is composed of a stent covered with a film and a hypotube (with appropriate connectors at the proximal end) which allows the manipulation of the funnel 3 while aspirating the thrombus 7 and during the device removal procedure, reducing the time required to perform the whole thrombectomy intervention. The thrombectomy device may be medium gauge, e.g., 6F (2 millimeter (mm)), without limitation of other sizes according to different needs of device dimensions related to different blood vessel 6 types and diameters. As should be clear the device may have different presentations to fulfill these different needs upon changing the maximum diameter that the self-expandable funnel 3 can reach. In any case, once moved outside the delivery catheter 1, the distal end of the funnel 3 will expand to the diameter of the artery 6 at that point.

As depicted in FIG. 5, in one embodiment the tapered dilator catheter 5, the aspiration funnel catheter 2, and the delivery catheter 1 are oriented along the same axis. This distribution minimizes transaxial forces over the funnel 3 and the combination of aspiration funnel catheter 2 and the delivery catheter 1. What is more, this distribution enables simultaneous manipulation of all device components. The positioning and operation of the device is assisted by fluoroscopy, and, therefore, the device includes some radiopaque markers.

Figure 6:
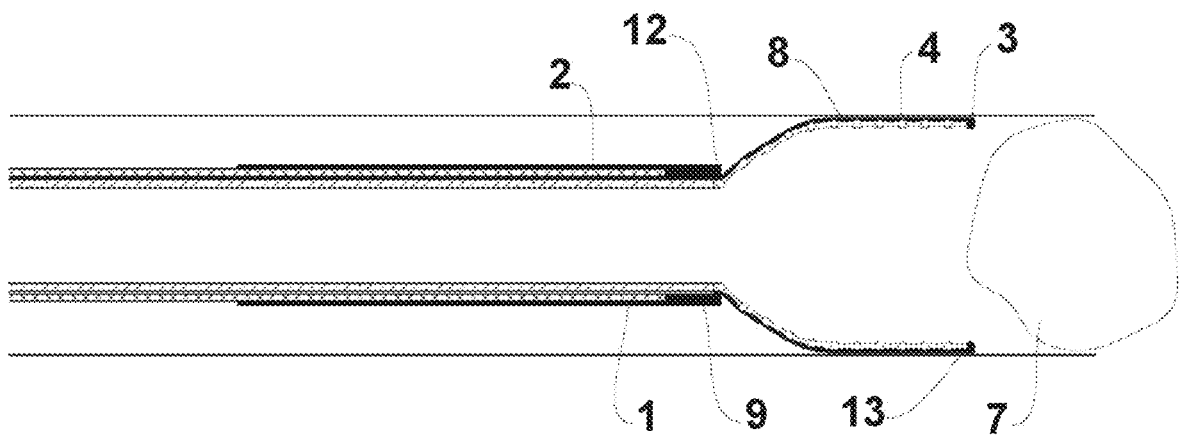
FIG. 6 is a schematic elevational view of the thrombectomy device according to the present invention depicting the entire device in its expanded configuration, including all the device components and depicting points with hydrophilic coating.
Figure 7A:
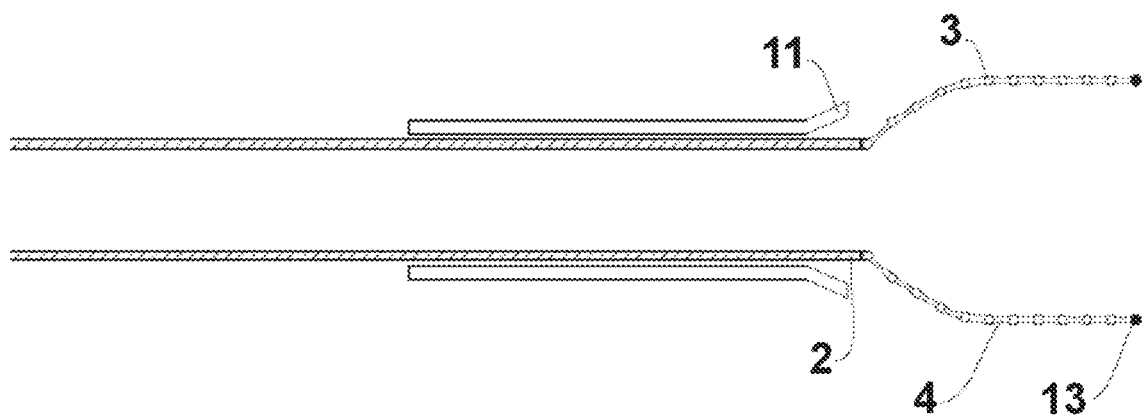
Figure 7B:
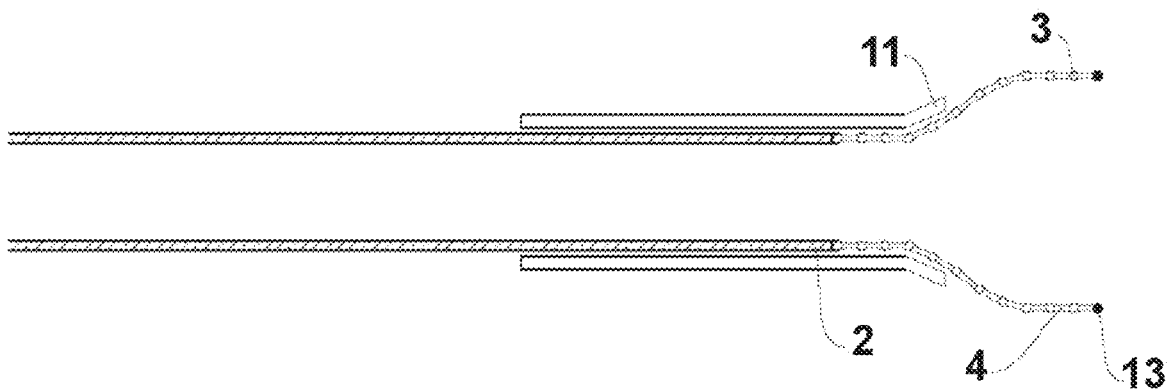

Referring to FIG. 6, to aspirate the thrombus 7, vacuum is applied through aspiration funnel catheter 2 and the delivery catheter 3: one or both of them. The said aspiration is exerted with an aspiration device which may be a syringe or aspiration pump at the proximal end of the catheters. On applying vacuum, the blood flow is reversed and the thrombus 7 is aspirated into the device.

In order to avoid any leak of the material of the thrombus 7, additionally to the vacuum applied along the device, the inner side of the aspiration funnel 2 can have any physical, chemical, biochemical, mechanical element or combination of them able to retain the thrombus 7 in any circumstances during the procedure. In one embodiment, the said holding system can be made of sharp physical elements such as spikes, skewers, saws, clamps or any combination of them.

At this point, all that remains is to withdraw the device together with the thrombus 7, maintaining the vacuum in the device. This is possible because the arterial system increases its diameter as we go down (e.g., from the cerebral arteries to the aorta), but in the case that a narrow passage is encountered, the funnel 3 is designed to encompass any dimensional change on the thrombus 7, avoiding any leak of thrombus material. While passing through the narrow passage, as the funnel 3 narrows proportionally it also lengthens allowing for the entire thrombus 7 to remain securely within the funnel 3. In the event that the aspiration funnel catheter 2 is removed from delivery catheter 1 by its proximal end, an optional resheathing element may allow the user to reintroduce the funnel 3 into the delivery catheter 1 before further use. Such resheathing element can be any special fixture appended to delivery catheter 1 or a standalone element which can be rigid or plastic. In one embodiment this element is a modification of the hemostatic valve of the delivery catheter 1 with an appropriate conic closure for closing the aspiration funnel 2 to the diameter of the hemostatic valve. In another preferred embodiment, the resheathing element is a cannula 11 or funnel with appropriate conical closure and diameter which can be rigid or plastic; if such element has plastic behavior, it can be adjusted to the hemostatic valve diameter and even inserted on its mouth for facilitate the resheathing.

FIG. 8 depicts a thrombectomy device of the present invention which allows for the automated maneuvering of the thrombectomy device through a vascular system.

The system comprises a radiographic marker 12 indicating the location of the thrombus 7 in an artery 6 and a radiographic marker 13 indicating the location of the thrombectomy device in the vascular system, an imaging device 20 which detects the radiographic markers, a communications channel 22 to provide means to transport the image to a control module 24, the control module 24 programmed to allow for guidance of the deployment of the thrombectomy device and storage of data on a data storage device 26, a means to communicate between the control module and the thrombectomy device, and an automated proximal device 30 which provides a guidance system to deploy the thrombectomy device. The control module may be a programmable logic controller, a computer, or the like. In one embodiment the control module 24 is guided by a computer assisted controller 28. The communications channel 22 can be Ethernet, WiFi, Bluetooth, or the like. The control module 24 is programmed to guide the physician or technician operating the thrombectomy device which allows for the thrombectomy device to be used in non-hospital settings such as nursing homes or assisted care living facilities.

By allowing the thrombectomy device to be used "in the field" the time required to perform the thrombectomy is greatly reduced significantly improving patient outcomes. The control may also be via a controller such as those in use in other current medical devices. In another preferred embodiment, the system may be controlled manually.

As should be readily apparent to those skilled in the art, the device of the present invention is a set of different catheters designed to be used combined as an unique device in one preferred sequence of actions. However its components or specific subsets of them could be used in different sequences than the one preferred and, even, separately or in combination with other devices.

For example, the tapered dilator catheter could be used for clearing the way through blood vessels to any lesion prior to using other devices than the one described on the present invention. Likewise, the subset of delivery catheter and aspiration funnel catheter can be used in combination with the kind of thrombectomy devices known as stent retrievers for securing the fixation of the thrombus and avoiding any leak of its material.

Device Manufacture

The individual components of the present invention may be assembled using techniques well known by those skilled in the art. Materials used for the device of the present invention are those of common use for those skilled in the art. Coatings and coverings of specific parts of the device are also those of common use and applied with well know techniques for those skilled in the art.

Method of Use

A method for using a thrombectomy device to extract vascular thrombi comprising the steps of introducing the thrombectomy device into a blood vessel, guiding the thrombectomy device to a proximal distance from a thrombus via a dilator catheter, positioning a guide catheter adjacent to the thrombus, deploying a funnel, aspirating the thrombus, encompassing the thrombus into the funnel while keeping thrombus materially intact, and removal of thrombectomy device and thrombus from blood vessel.

While only certain features and embodiments of the invention have been shown and described, many modifications and changes may occur to those skilled in the art (e.g., variations in sizes, dimensions, structures, shapes and proportions of the various elements, values of parameters (e.g., temperatures, pressures, etc.), mounting arrangements, use of materials, colors, orientations, etc.) without materially departing from the novel teachings and advantages of the subject matter recited in the claims. The order or sequence of any process or method steps may be varied or re-sequenced according to alternative embodiments. It is, therefore, to be understood that the appended claims are intended to cover all such modifications and changes as fall within the true spirit of the invention. Furthermore, in an effort to provide a concise description of the exemplary embodiments, all features of an actual implementation may not have been described (i.e., those unrelated to the presently contemplated best mode of carrying out the invention, or those unrelated to enabling the claimed invention). It should be appreciated that in the development of any such actual implementation, as in any engineering or design project, numerous implementation specific decisions may be made. Such a development effort might be complex and time consuming, but would nevertheless be a routine undertaking of design, fabrication, and manufacture for those of ordinary skill having the benefit of this disclosure, without undue experimentation.

What is claimed is:

1. A thrombectomy device comprising:
   a delivery catheter;
   a self-expandable funnel configured to be movably disposed within the delivery catheter in a retracted position and at least partially outside the delivery catheter in an extended position, the self-expandable funnel comprising a shape memory material with a non-permeable covering of one or more biocompatible materials, a diameter of a distal end of the self-expandable funnel being greater in the extended position than in the retracted position, the self-expandable funnel in its extended position being configured to adapt its shape and length to a surrounding blood vessel such that the self-expandable funnel expands to a diameter of the blood vessel wherein the self-expandable funnel length increases as the diameter decreases to retain a thrombus within the self-expandable funnel during movement of the self-expandable funnel through the blood vessel while a proximal portion of the self-expandable funnel and the non-permeable covering of the self-expandable funnel occludes the blood vessel; and an aspiration funnel catheter having a distal end and a proximal end, the distal end connected to a proximal end of the self-expandable funnel and the proximal end in communication with an aspiration device configured to aspirate the retained thrombus within the funnel.

2. The thrombectomy device of claim 1 further comprising a tapered dilator catheter configured to be movably disposed within the delivery catheter, wherein the self-expandable funnel is configured to remain within the delivery catheter after the dilator catheter has been removed.

3. The thrombectomy device of claim 2 wherein the delivery catheter, the dilator catheter, the aspiration funnel catheter and the self-expandable funnel are oriented on the same axis.

4. The thrombectomy device of claim 1 wherein the shape memory material comprises nitinol.

5. The thrombectomy device of claim 1 wherein the self-expandable funnel has a diameter at its distal end of between 2 millimeters and 15 millimeters.

6. The thrombectomy device of claim 1 wherein the self-expandable funnel comprises a thrombus retaining element.

7. The thrombectomy device of claim 6 wherein the thrombus retaining element comprises a sharp physical element.

8. The thrombectomy device of claim 1 wherein the delivery catheter and the self-expandable funnel are oriented on the same axis.

9. The thrombectomy device of claim 1 further comprising a resheathing element adapted to reintroduce the self-expandable funnel into the delivery catheter.

10. The thrombectomy device of claim 9 wherein the resheathing element comprises a cannula, a clamp, a funnel, or any combination of them.

11. The thrombectomy device of claim 1 wherein the aspiration funnel catheter extends proximally from a proximal opening of the self-expandable funnel, the aspiration funnel catheter being configured to aspirate the thrombus within the self-expandable funnel.

12. A system for extraction of vascular thrombi from a blood vessel comprising the thrombectomy device of claim 1, wherein the system further comprises a communications channel, a control module, a data storage device, and a guidance system, wherein the control module is guided by a computer-assisted controller.

13. The system according to claim 12, further comprising an imaging device, a first radiomarker, and a second radiomarker, wherein the first radiomarker is arranged and configured to indicate a location of the distal end of the self-expandable funnel, and the second radiomarker is arranged and configured to indicate a location of the thrombus.

14. The thrombectomy device of claim 1 wherein the one or more biocompatible materials of the non-permeable covering comprises a biocompatible elastomeric polymer, a durable biocompatible polyurethane with elastomeric behavior or an ePTFE with the polymer fibers oriented parallel to the direction of length of the delivery catheter.

15. A thrombectomy device comprising:

a delivery catheter; and an expandable aspiration member having a proximal end and a distal end, the proximal end in communication with an aspiration device and the distal end comprising a self-expandable structure formed of a shape memory material with a non-permeable covering comprising one or more biocompatible elastomeric materials, the aspiration member configured to be movably disposed within the delivery catheter in a retracted position maintaining a generally cylindrically shaped distal most portion and when deployed outside the delivery catheter in an extended position in use within a blood vessel, the distal most portion of the aspiration member being configured to self-expand wherein a diameter of the distal most portion of the aspiration member is greater in the extended position than in the retracted position, the self-expandable structure in the distal most portion of the aspiration member being configured to adapt its shape and length to a surrounding blood vessel such that the distal most portion of the aspiration member expands to a diameter of the blood vessel and a tapered portion of the self-expandable structure and the non-permeable covering adjacent to a distal end of the delivery catheter occludes the blood vessel wherein the distal most portion of the aspiration member length increases as the diameter decreases to retain a thrombus within the distal most portion of the aspiration member during proximal movement of the aspiration member through the blood vessel.

16. The thrombectomy device of claim 15 further comprising a tapered dilator catheter configured to be movably disposed within the delivery catheter, wherein the aspiration member is configured to remain within the delivery catheter after the dilator catheter has been removed.

17. The thrombectomy device of claim 16 wherein the delivery catheter, dilator catheter and aspiration member are oriented on the same axis.

18. The thrombectomy device of claim 15 wherein the shape memory material comprises nitinol.

19. The thrombectomy device of claim 15 wherein the aspiration member in its extended position has a diameter at its distal end of between 2 millimeters and 15 millimeters.

20. The thrombectomy device of claim 15 wherein the aspiration member comprises a thrombus retaining element.

21. The thrombectomy device of claim 20 wherein the thrombus retaining element comprises a sharp physical element.

22. The thrombectomy device of claim 15 wherein the delivery catheter and aspiration member are oriented on the same axis.

23. The thrombectomy device of claim 15 further comprising a resheathing element adapted to reintroduce the aspiration member into the delivery catheter.

24. The thrombectomy device of claim 23 wherein the resheathing element comprises a cannula, a clamp, a funnel, or any combination of them.

25. A system for extraction of vascular thrombi from a blood vessel comprising the thrombectomy device of claim 15, wherein the system further comprises a communications channel, a control module, a data storage device, and a guidance system, wherein the control module is guided by a computer-assisted controller.

26. The system according to claim 25, further comprising an imaging device, a first radiomarker, and a second radiomarker, wherein the first radiomarker is arranged and configured to indicate a location of the distal end of the aspiration member, and the second radiomarker is arranged and configured to indicate a location of the thrombus.

27. The thrombectomy device of claim 15 wherein the aspiration member further comprises a tube extending proximally from a proximal opening of the distal portion of the aspiration member, the aspiration member being further configured to aspirate and capture the thrombus.

* * * * *